United States Patent
Boehm et al.

(10) Patent No.: US 10,258,441 B2
(45) Date of Patent: Apr. 16, 2019

(54) METHOD FOR PRODUCING A DENTAL PROSTHESIS

(71) Applicant: Heraeus Kulzer GmbH, Hanau (DE)

(72) Inventors: Uwe Boehm, Hanau (DE); Klaus Ruppert, Maintal (DE); Stephan Dekert, Wehrheim/Obernhain (DE)

(73) Assignee: Heraeus Kulzer GmbH, Hanau (DE)

( * ) Notice: Subject to any disclaimer, the term of this patent is extended or adjusted under 35 U.S.C. 154(b) by 108 days.

(21) Appl. No.: 15/323,137

(22) PCT Filed: Jul. 3, 2015

(86) PCT No.: PCT/EP2015/065232
§ 371 (c)(1),
(2) Date: Dec. 30, 2016

(87) PCT Pub. No.: WO2016/005287
PCT Pub. Date: Jan. 14, 2016

(65) Prior Publication Data
US 2017/0135790 A1    May 18, 2017

(30) Foreign Application Priority Data
Jul. 9, 2014 (DE) .......... 10 2014 109 563

(51) Int. Cl.
*A61C 13/10*    (2006.01)
*A61C 13/36*    (2006.01)
(Continued)

(52) U.S. Cl.
CPC ...... *A61C 13/1016* (2013.01); *A61C 13/0004* (2013.01); *A61C 13/0006* (2013.01);
(Continued)

(58) Field of Classification Search
CPC .............. A61C 13/101; A61C 13/0004; A61C 13/0006; A61C 13/0022; A61C 13/01;
(Continued)

(56) References Cited

U.S. PATENT DOCUMENTS 1,518,075 A * 12/1924 Kesling ............... A61C 11/022
33/513
2,641,802 A    6/1953 Grant
(Continued)

FOREIGN PATENT DOCUMENTS

DE    19739220 C2    5/2002
DE    10304757 A1    8/2004
(Continued)

OTHER PUBLICATIONS

Office Action in German Application No. 10 2014 109 563.4 dated May 6, 2015, 6 pages.
(Continued)

*Primary Examiner* — Nicholas D Lucchesi
(74) *Attorney, Agent, or Firm* — Marshall, Gerstein & Borun LLP

(57) ABSTRACT

The invention relates to a process for producing a dental prosthesis with the chronological steps:
A) Inserting the prosthetic teeth into the prosthetic base and connecting them with it in such a way that after their insertion into the prosthetic base the prosthetic teeth have limited movability in the prosthetic base
B) Changing the position and/or the orientation of at least one prosthetic tooth in the prosthetic base;
C) Fixing the prosthetic teeth on the coronal side in a key, and securing the orientation and position of the prosthetic teeth to one another in the changed position and/or orientation;
D) Separating the prosthetic teeth from the prosthetic base;
F) Fastening the prosthetic teeth in the prosthetic base with a cement or an adhesive, the gaps between the surfaces of the prosthetic base that are provided for fixation of the prosthetic teeth and the prosthetic teeth being filled with the cement or the adhesive; and
(Continued)

Figure 1:

G) Allowing the cement or adhesive to harden, the prosthetic teeth being solidly connected with the prosthetic base, so that the orientation and position of the prosthetic teeth to one another and to the prosthetic base is fixed, and separating the key from the prosthetic teeth. The invention also relates to a dental prosthesis produced using such a process and a kit to carry out such a process.

17 Claims, 2 Drawing Sheets

(51) Int. Cl.
    *A61C 13/00*     (2006.01)
    *A61C 13/01*     (2006.01)
    *A61C 13/08*     (2006.01)
    *A61C 13/093*     (2006.01)

(52) U.S. Cl.
    CPC .......... *A61C 13/0022* (2013.01); *A61C 13/01* (2013.01); *A61C 13/08* (2013.01); *A61C 13/10* (2013.01); *A61C 13/1006* (2013.01)

(58) Field of Classification Search
    CPC ... A61C 13/08; A61C 13/10066; A61C 13/10; A61C 13/1006
    See application file for complete search history.

(56) References Cited

U.S. PATENT DOCUMENTS

| | | | | |
|---|---|---|---|---|
| 3,644,996 | A * | 2/1972 | Weinkle | A61C 13/04 433/171 |
| 3,971,133 | A * | 7/1976 | Mushabac | A61C 13/0016 433/213 |
| 4,161,065 | A * | 7/1979 | Gigante | A61C 13/1013 264/18 |
| 4,457,713 | A * | 7/1984 | Schneider | A61C 13/0001 264/18 |
| 4,470,815 | A * | 9/1984 | Hazar | A61C 13/00 264/18 |
| 4,681,543 | A | 7/1987 | Monroy | |
| 6,039,566 | A | 3/2000 | Foser | |
| 8,506,299 | B2 | 8/2013 | Gartner et al. | |
| 2011/0236856 | A1 | 9/2011 | Kanazawa et al. | |
| 2012/0258430 | A1 | 10/2012 | Ruppert et al. | |
| 2013/0108988 | A1 | 5/2013 | Simoncic | |
| 2014/0239527 | A1 * | 8/2014 | Lee | A61K 6/083 264/17 |
| 2016/0193019 | A1 | 7/2016 | Heinz et al. | |

FOREIGN PATENT DOCUMENTS

| | | |
|---|---|---|
| DE | 102009056752 A1 | 6/2011 |
| EP | 2742906 A1 | 6/2014 |
| WO | WO-91/07141 A1 | 5/1991 |
| WO | WO-2012/021816 A2 | 2/2012 |
| WO | WO-2013/124452 A1 | 8/2013 |

OTHER PUBLICATIONS

Search Report in International Application No. PCT/EP2015/065232 dated Sep. 1, 2015, 6 pages.

International Preliminary Report on Patentability and Written Opinion in International Application No. PCT/EP2015/065232 dated Jan. 10, 2017, 12 pages.

* cited by examiner

METHOD FOR PRODUCING A DENTAL PROSTHESIS

The invention relates to a process for producing a dental prosthesis from a prosthetic base and multiple prosthetic teeth. The invention also relates to a dental prosthesis produced using such a process and a kit to carry out such a process.

Dental prostheses are commonly created using an analog process. That is, at the present time the prosthetic base is usually produced using a an analog process that involves first making an impression of the toothless jaw of the patient. This impression is used to make a mold, which is filled with a gum-colored plastic. After the plastic hardens, it is finished to give it the desired shape. Then, the prosthetic teeth are inserted into the hollow mold and connected with the prosthetic base during the molding process.

To produce the dental prosthesis, prosthetic teeth are manually set, one by one, on a wax base on a plaster model of the toothless jaw. In the next step, this wax prosthesis is put in a cell and embedded in plaster, silicone, or gel (depending on the later processing technique), and after the embedding material hardens the wax base is then washed out with hot water to create a hollow space for the plastic for the prosthesis. In the process, the prosthetic teeth remain in the embedding material. An appropriate plastic is injected or poured into the hollow space, and after the plastic hardens the dental prosthesis is obtained. When the fabricated teeth are installed, the dental technician and possibly also the dentist adapts them to the situation in the mouth of the respective patient, and grinds them.

WO 91/07141 A1 discloses a process for producing a dental prosthesis, this process involving milling a prosthetic base out of a plastic block based on an impression.

In addition to manual techniques, digital manufacturing methods are becoming more and more important in the dental area. For some years, replacement teeth, such as, e.g., crowns and bridges, have been produced by means of subtractive milling processes using CAD-CAM technologies (CAM—Computer-Aided Manufacturing, CAD—Computer-Aided Design).

In addition, generative methods such as SLM (Selective Laser Melting) are becoming more and more important for producing crowns, bridges, and models, and stereolithography and DLP (Digital Light Processing) are becoming more and more important for polymer-based dental products such as, for example, temporary dentures, prostheses, orthodontic appliances, mouth guards, drilling templates, or dental models. So far, the production of acrylic-based dentures by means of rapid prototyping (RP) techniques is still subject to strong limitations. So far, high-quality and esthetic dentures that are multicolored or made of different polymer materials (for example, for the enamel and dentin masses) can only be produced by means of expensive RP machines with multiple material chambers, or by means of elaborate cementing and joining techniques.

Likewise, the production of material combinations (for example, cobalt-chromium and polymer) by means of RP techniques has been very expensive and not commercially viable up to now.

There are already first processes, such as, for example, the processes disclosed in DE 10 2009 056 752 A1 or WO 2013 124 452 A1, which involve digital setup of a partial or total dental prosthesis and production through CAD-CAM processes. DE 103 04 757 B4 discloses a process for producing dentures, in which the teeth are virtually set up in a virtual model and a prosthetic base is produced on the basis of the virtual model.

Such processes have the disadvantage that the dentist or dental technician using them must expend greater effort to make small corrections in the position and orientation of the prosthetic teeth in the prosthetic base. It is necessary to machine the occlusal surface of the prosthetic teeth, or to remove them and then grind the prosthetic base or grind the basal surface of the prosthetic teeth to adjust their position and orientation. Thus, the goal of the invention is to overcome the disadvantages of the prior art. In particular, the goal is to provide a process that allows the dentist or user to make a simple correction in the position and orientation of the prosthetic teeth in the prosthetic base, to make it simple to adapt the dental prosthesis to the needs of the patient. In addition, it should make production of the prosthetic base, and thus the dental prosthesis, as simple, complete, and economical as possible.

The goals of the invention are achieved by a process for producing a dental prosthesis from a prosthetic base and multiple prosthetic teeth with the following chronological steps:

A) Inserting the prosthetic teeth into the prosthetic base and connecting them with it in such a way that after insertion of the prosthetic teeth into the prosthetic base the prosthetic teeth have limited movability in the prosthetic base, the surfaces of the prosthetic base which are provided for fixation of the prosthetic teeth being larger than the corresponding basal surfaces of the prosthetic teeth, so that the prosthetic teeth are movable to a limited extent in the prosthetic base;

B) Changing the position and/or the orientation of at least one prosthetic tooth in the prosthetic base;

C) Fixing the prosthetic teeth on the coronal side in a key, and securing the orientation and position of the prosthetic teeth to one another in the changed position and/or orientation;

D) Separating the prosthetic teeth from the prosthetic base;

F) Fastening the prosthetic teeth in the prosthetic base with a cement or an adhesive, wherein the gaps between the surfaces of the prosthetic base that are provided for fixation of the prosthetic teeth and the prosthetic teeth being filled with the cement or the adhesive; and G) The cement or adhesive is hardening or is being hardened, whereby the prosthetic teeth being solidly connected with the prosthetic base, so that the orientation and position of the prosthetic teeth to one another and to the prosthetic base is fixed, and separating the key from the prosthetic teeth.

In this invention, a key is understood to be a material or device which fixes the position and orientation of the prosthetic teeth relative to one another, without their position or orientation to one another still changing after their position and/or orientation in the prosthetic base is changed. Preferably, a silicone mass can be used as a key for this purpose.

The term "coronal" (from Latin corona "crown") means on the dental crown and toward the dental crown as a positional and directional term on the teeth, comprising the occlusal surface and the peripheral areas of the tooth prosthesis surrounding the occlusal surface. In this connection, limited movability means that the prosthetic teeth can be moved in the prosthetic base, but are not completely freely movable. The inserted prosthetic teeth can then be rotated or tilted by a few degrees or be displaced by a few tenths of a millimeter with respect to the prosthetic base in the surfaces of the prosthetic base that are provided for fixation of the prosthetic teeth.

The cement or adhesive can be hardened by allowing a sufficiently long period of time to pass. During hardening, chemical reactions take place which lead to the hardening of the cement or glue. The hardening can be actively supported by drying or, for example, by an increased temperature.

The prosthetic teeth and/or the prosthetic base preferably consist of a plastic, especially preferably polymethylmethacrylate (PMMA).

The prosthetic teeth can be individual and/or joined together in multiple groups or joined together in complete dental arches. Prosthetic teeth that are joined together are solidly connected with one another.

The inventive process can preferably provide that before step A) a thick, fluid mass, preferably a wax or a modeling clay, being applied to the prosthetic base surfaces provided for fixation of the prosthetic teeth and/or the basal surfaces of the prosthetic teeth, which is arranged, after the insertion of the prosthetic teeth in step A), between the prosthetic teeth and the prosthetic base surfaces that are provided for fixation of the prosthetic teeth, so that the position and/or orientation of the prosthetic teeth in the prosthetic base is changeable by deformation of the thick, fluid mass, in particular the wax or the modeling clay.

The thick fluid mass, that is such a wax, preferably sticky wax, or the modeling clay, must on the one hand be soft enough at room temperature (or slightly above it) to allow the position and orientation of the prosthetic teeth to be changed, and on the other hand the position and orientation of the prosthetic teeth in the prosthetic base must not change due to their own weight. In addition, the thick, fluid mass should preferably have a certain adhesive strength. The adhesive strength or adhesion must be sufficient to hold the tooth prostheses so that they cannot come loose from the thick, fluid mass.

To accomplish this, the thick, fluid mass preferably has a viscosity between $10^2$ Pa·s and $10^6$ Pa·s. The thick, fluid mass, in particular the wax or the modeling clay, is arranged between the prosthetic teeth and the prosthetic base, and can be shaped by hand. This means that the prosthetic teeth can be moved in the prosthetic base, but hold their position without another force acting on them. This makes it easy for the dentist or the user to change the position and orientation of the prosthetic teeth in the prosthetic base by hand.

This measure makes it especially simple to position and orient the prosthetic teeth in the prosthetic base.

After the thick, fluid mass, in particular the wax or the modeling clay, is used, that is, after the position and/or orientation of the prosthetic teeth in the prosthetic base is corrected and the prosthetic teeth are removed from the prosthetic base, it should be as easy as possible to remove it without residue from the prosthetic teeth and the prosthetic base.

Such processes can provide that after step D) and before step F) the thick, fluid mass, in particular the wax or the modeling clay, be removed from the prosthetic teeth and/or the surfaces of the prosthetic base that are provided for fixation of the prosthetic teeth, preferably washed off with hot water or removed with steam.

Preferably, the entire prosthetic base is, and/or all the prosthetic teeth are cleaned of the thick, fluid mass, in particular the wax or the modeling clay.

The surfaces of the prosthetic teeth and/or the prosthetic base are cleaned of the thick, fluid mass, in particular the wax or the modeling clay, to allow a stable bond to be achieved during the subsequent final fastening of the prosthetic teeth in the prosthetic base. This allows a dental prosthesis to be stable even for a long time.

A further development of the inventive process proposes that the prosthetic base and/or the prosthetic teeth is or are produced and/or machined with a CAM process or a rapid prototyping process.

This invention uses the generally known term rapid prototyping process for a manufacturing process in which the prosthetic base and/or the prosthetic teeth is or are produced with a manufacturing process commonly used for rapid prototyping. Since the prosthetic base and/or the prosthetic teeth are not prototypes but rather semi-finished components, the terms "rapid manufacturing", "3D printing", "rapid product development", "advanced digital manufacturing", or "e-manufacturing" that are occasionally used in such connections could also be used instead of the term "rapid prototyping process". The prosthetic base is preferably made of a rose-colored or pink plastic and the prosthetic teeth are made of a tooth-colored plastic.

Combining the manufacturing process with a CAM or RP process for production or machining of the prosthetic base and/or the prosthetic teeth has the advantage that the play between the surface for fixation of the prosthetic teeth with the prosthetic base and the basal supporting surfaces of the prosthetic teeth, play which is necessary for the movability of the prosthetic teeth in the prosthetic base in step B), can immediately be taken into consideration by computation in the framework of a CAD process, and then automatically taken into consideration through the CAM process or RP process during production.

Preferably, it can be provided in step B) that the change in position and/or orientation of at least one prosthetic tooth in the prosthetic base is done directly by adaptation to the patient.

This makes it clear that the change in position the and/or alignment or orientation of the prosthetic teeth should be done for adaptation to the anatomical conditions in the oral cavity of the patient.

A further development of the inventive process can provide, in a step E) between steps D) and F), that at least areas of the exposed surfaces of the prosthetic teeth are swollen with a solvent and/or at least areas of the surfaces of the prosthetic base that are provided for fixation of the prosthetic teeth are swollen with a solvent.

This achieves an especially stable connection of the prosthetic teeth with the prosthetic base. The swelling makes the surfaces liquid or fluid, so that during a subsequent cementing process these areas will reharden, thus producing a more stable connection through a greater thickness of the prosthetic material.

An especially preferred further development of the process can further provide, in step E), that at least areas of the exposed surfaces of the prosthetic teeth are roughened and swollen with a solvent and/or at least areas of the surfaces of the prosthetic base that are provided for fixation of the prosthetic teeth are roughened and swollen with a solvent.

The additional roughening or slight roughening of the surfaces allows the solvent to solvate the surfaces more quickly. The roughening or slight roughening of the surface can be done by the solvent. In addition, the effective surface for bonding through the cement or the glue is enlarged, and thus the prosthetic teeth are better held in the prosthetic base, improving the durability of the dental prosthesis. Further, the inventive prosthetic teeth and prosthetic base can be cleaned with hot water or steam.

It is especially advantageously to use inventive process, since it provides that the surfaces of the prosthetic base that are provided for fixation of the prosthetic teeth are larger than the corresponding basal surfaces of the prosthetic teeth (that is, larger than the corresponding basal surfaces of the prosthetic teeth that are intended to lie on the surfaces of the prosthetic base), so that the prosthetic teeth have limited movability in the prosthetic base. Preferably, it can be provided that the prosthetic teeth are tiltable and/or rotatable by up to 5°, and/or their position is displaceable by up to 1 mm in the prosthetic base. Here rotation refers to rotation about the longitudinal axis of the prosthetic teeth and tilting refers to rotation about an axis perpendicular to the longitudinal axis.

This creates the necessary gaps for movability of the prosthetic teeth in the prosthetic base, which according to the invention are preferably filled, at least in areas, with the thick, fluid mass, in particular the wax or the modeling clay, to stabilize the position and orientation of the prosthetic teeth.

Furthermore, it can be provided that the key used in step C) is a silicone key.

Silicone keys, for example a silicone mass, have suitable mechanical properties to hold the prosthetic teeth in the desired new position.

Preferably, the inventive process can provide that the excess quantities of cement or adhesive are removed after the hardening.

A further development also proposes using a self-hardening cement paste as cement, preferably using a cement paste made from a powder and a liquid, especially preferably using a polymethylmethacrylate cement dough.

This allows an especially stable and simple connection to be made between the prosthetic teeth and the prosthetic base. It is especially preferable for cements to have a short swelling time and to harden free of bubbles. It is preferable for the cement to harden at room temperature and without increased pressure. In particular, the cement Paladur® of the company Heraeus Kulzer GmbH has especially proven itself.

The cement or glue for final fixation of the prosthetic teeth in the prosthetic base should be non-toxic, volume-filling, color-stable, durable in compound, resistant to hydrolysis, and volume-stable when it hardens, and have a suitable color that is stable over a long time. Cements that are also possible for this purpose in addition to PMMA cements such as Paladur® of the Heraeus Kulzer GmbH are Versyo® of Heraeus Kulzer GmbH, Signum composit Flow® of Heraeus Kulzer GmbH, or other PMMA-based cements.

As a glue, it is possible to use, for example, a super glue or an adhesive that is also suitable for filling the volume of the gaps between the prosthetic base and the prosthetic teeth.

The invention can also provide that before step A) a partial dental prosthesis or a total dental prosthesis is digitally designed using a CAD process and decomposed by means of file-splitting into a virtual model of a prosthetic base and a virtual model of the prosthetic teeth, the prosthetic base and/or the prosthetic teeth being produced by means of a CAM process on the basis of the virtual models.

This allows automation of the process, which can be achieved with CAD-CAM processes.

Preferably it can also be provided that a methyl methacrylate-containing liquid is used as a solvent.

Alternatively, it is also possible to use a ketone such as acetone, or an alcohol as a solvent. However, methyl methacrylate-containing liquids are substantially more suitable to swell the PMMA in prosthetic teeth and prosthetic bases made of PMMA.

These solvents are especially suitable for swelling the materials that are especially preferably used for production of the prosthetic base and the prosthetic teeth.

The goals on which the invention is based are also achieved by a dental prosthesis produced with such a process.

Furthermore, the goals on which the invention is based are achieved by a kit for carrying out such a process, this kit comprising a key for fixing the prosthetic teeth oriented in a prosthetic base and a solvent for swelling the prosthetic teeth and/or the prosthetic base, preferably an MMA-containing liquid.

It can be provided that the kit comprises a thick, fluid mass, in particular a wax or a modeling clay, which is provided for movable arrangement of the prosthetic teeth in the prosthetic base.

It can also be provided that the kit comprises a cement or an adhesive for fixing the prosthetic teeth in the prosthetic base.

Finally, it can also be provided that the kit comprises multiple prefabricated prosthetic teeth and/or at least one prosthetic base blank.

The prosthetic teeth can also be in the form of groups or complete prosthetic dental arches, which are solidly connected with one another. In the latter case, it is then only still possible to adjust the orientation and position of the prosthetic dental arches with respect to the prosthetic base or the prosthetic dental arches with respect to one another.

The invention is based on the surprising finding that the process succeeds in making the position and orientation of the prosthetic teeth minimally changeable and then making it simple to perform the final steps to produce the dental prosthesis. A decisive step for accomplishing this is to use the key. The key allows to fix the orientation and position of the prosthetic teeth or the groups of prosthetic teeth relative to one another, so that the desired and previously corrected orientation and position of the prosthetic teeth relative to one another or the groups of prosthetic teeth relative to one another is preserved during the later insertion into the prosthetic base. For implementation of the process it is important or especially advantageous for a gap to be provided as play between the surfaces for fixation of the prosthetic teeth in or on the prosthetic base, and for this gap to be filled with a thick, fluid mass for free and temporarily stable positioning of the prosthetic teeth in the prosthetic base.

The swelling of the surfaces of the prosthetic teeth and/or the surfaces of the prosthetic base that are provided for fixation of the prosthetic teeth makes it possible to achieve an especially stable connection of the prosthetic teeth with the prosthetic base. The prosthetic teeth and/or the prosthetic base are preferably swollen using methyl methacrylate (MMA) or a solution containing MMA. The prosthetic teeth preferably consist of highly cross-linked PMMA. Solvation of the PMMA material involves the MMA solvating the PMMA and penetrating it, which softens the material. This produces a solvated layer that stabilizes the connection when the final connection of the prosthetic teeth is then made with the prosthetic base using with the help of a preferably used PMMA cement or glue. According to the invention this achieves an especially stable connection of the prosthetic teeth with the prosthetic base.

Sample embodiments of the invention are explained below using two schematically illustrated figures, without, however, this limiting the invention. The figures are as follows:

FIG. 1: A perspective view of a prosthetic base for a lower jaw to carry out an inventive process; and FIG. 2: A perspective view of prosthetic teeth to carry out an inventive process for insertion into the prosthetic base according to FIG. 1.

FIG. 1 shows perspective view of a prosthetic base 1 for a lower jaw to carry out an inventive process. The prosthetic base consists of a rose-colored plastic. The coloring and transparency are suitably selected to give the appearance of gums. The top of the prosthetic base 1 has multiple surfaces 2 for fixation of prosthetic teeth (not shown in FIG. 1).

Figure 2:
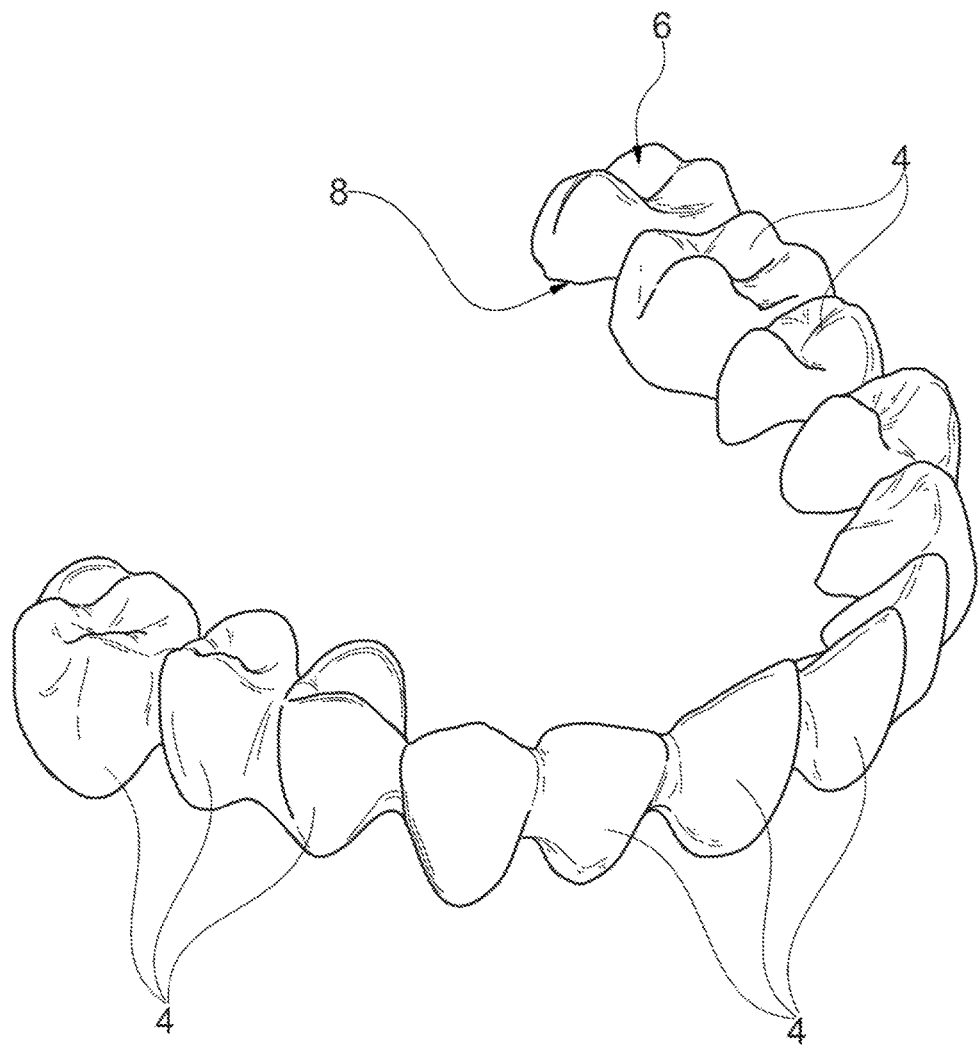

FIG. 2 shows a perspective view of prosthetic teeth 4 to carry out an inventive process, which are provided for insertion into the prosthetic base 1 according to FIG. 1. It should be pointed out that the prosthetic teeth 4 are preferably detached, not connected with one another, as is shown in FIG. 2. However, the process can also be carried out with dental arches of prosthetic teeth 4 that are connected with one another, all of these dental arches or groups of them being connected with one another.

The prosthetic teeth 4 consist of a hard white plastic with a coloring and transparency that are suitable for teeth, or that match the patient's teeth. Every prosthetic tooth 4 has a coronal surface 6 (chewing surface) and a basal surface 8. The basal surface 8 is fixed in the surfaces 2 for fixation of the prosthetic teeth 4 in the prosthetic base 1. The surfaces 2 have an indexing, so that the prosthetic teeth 4 can only be inserted in one specific orientation in the prosthetic base and every prosthetic tooth 4 only fits to one surface 2.

The surfaces 2 are somewhat larger than the basal counterparts on the basal side 8 of the prosthetic teeth 4. Before the prosthetic teeth 4 are first inserted onto the surfaces 2 on the prosthetic base 1, a thin defined wax layer (not shown) is applied to the basal side 8 of the prosthetic teeth 4 and/or the surfaces 2 for fixation of the prosthetic teeth 4 in the prosthetic base 1. After insertion of the prosthetic teeth 4, the wax layer is then arranged between the prosthetic base 1 and the prosthetic teeth 4. This makes the inserted prosthetic teeth 4 slightly movable in the prosthetic base 1, thus allowing the dentist or the user to make a minimal correction in the position and orientation of the prosthetic teeth 4 in the prosthetic base 1. This allows the position and the orientation of the prosthetic teeth 4 in the prosthetic base 1 to be adapted to the needs of a patient for whom the dental prosthesis to be produced is intended. The data necessary for orientation and positioning of the prosthetic teeth 4 is obtained directly on the patient or with the help of CAD processes and/or pictures (3D scans), or with the help of articulators and impressions. The simplest possibility is to insert the prosthetic base 1 with the inserted prosthetic teeth 4 into the patient's oral cavity and adapt the position to the situation there.

After the position and orientation of the prosthetic teeth 4 in the prosthetic base 1 have been adapted, the prosthetic teeth 4 are fixed with a silicone key (not shown) by embedding the prosthetic teeth 4 in a silicone mass. The prosthetic teeth 4 may not be mechanically stressed to such an extent that their orientation or position is changed. Then, the prosthetic teeth 4 are removed from the prosthetic base 1.

The wax layer is removed from the prosthetic teeth 4 and from the prosthetic base 1. This can be done, for example, by washing it off with hot water or with steam. The basal side 8 of the prosthetic teeth 4 is roughened (for example, mechanically by sand jets or chemically with a suitable solvent) and swollen with a liquid containing methyl methacrylate (MMA). In the same way, the surfaces 2 for fixation of the prosthetic teeth 4 in the prosthetic base 1 are roughed up and swollen with an MMA-containing liquid. An MMA-containing liquid that can be used is, for example, Palabond® of the company Heraeus Kulzer GmbH.

After preassembling of the surfaces to be connected in this way, the prosthetic teeth 4 undergo their final cementing in the prosthetic base 1, while still remaining fixed in the silicone key at first. The cementing is done using an excess of cement, so that the gaps between the surfaces 2 for fixation of the prosthetic teeth 4 in the prosthetic base 1 and the prosthetic teeth 4, which were previously filled with the wax, are filled with the cement without basal hollow spaces remaining in the gaps and without edge gaps remaining in the area of the gingiva/neck of tooth of the dental prosthesis that is produced. In addition, the excess optimally wets the contact surfaces. Pushed out remnants of excess cement paste can be removed before and/or after hardening.

For final cementing of the prosthetic teeth 4 in the prosthetic base 1, a self-hardening powder/liquid-based cement is used. Light-hardening cements or adhesives usually do not show sufficient adhesiveness, since the light can only penetrate into the edge areas of the gaps between the prosthetic teeth 4 and the prosthetic base 1.

Powder/liquid-based prosthetic materials hardening at room temperature, such as, for example, the product Paladur® of Heraeus Kulzer GmbH, are especially suitable due to the rapid swelling time and the bubble-free hardening at room temperature even without autoclave (that is, without excess pressure).

However, other hardening combinations are also conceivable, for example with a dual hardening cement. This involves briefly fixing the teeth by means of light and performing the final hardening through a redox reaction.

The process according to the invention can be carried out with prosthetic bases 1 that are produced manually or by means of a rapid-prototyping process. In the same way, the process can also be applied to printed prosthetic teeth or prosthetic dental arches.

The inventive features disclosed in the preceding description, as well as in the claims, figures, and sample embodiments can be essential for implementing the invention in its various embodiments; this is true both for each individual feature and also for any combination of features.

LIST OF REFERENCE NUMBERS

1 Prosthetic base
2 Surface for fixation of prosthetic teeth
4 Prosthetic tooth
6 Coronal surface of prosthetic tooth
8 Basal surface of prosthetic tooth

The invention claimed is:

1. A process for producing a dental prosthesis from a prosthetic base and multiple prosthetic teeth, comprising the following chronological steps:
  A) inserting the prosthetic teeth into the prosthetic base and connecting them with the prosthetic base in such a way that after insertion of the prosthetic teeth into the prosthetic base the prosthetic teeth have limited movability in the prosthetic base, surfaces of the prosthetic base which are provided for fixation of the prosthetic teeth being larger than corresponding basal surfaces of the prosthetic teeth, so that the prosthetic teeth are movable to a limited extent in the prosthetic base;

B) changing the position and/or the orientation of at least one prosthetic tooth in the prosthetic base;

C) fixing the prosthetic teeth on the coronal side in a key, and securing the orientation and position of the prosthetic teeth to one another in the changed position and/or orientation;

D) separating the prosthetic teeth from the prosthetic base;

F) fastening the prosthetic teeth in the prosthetic base with a cement or an adhesive, wherein gaps between the surfaces of the prosthetic base and the prosthetic teeth are filled with the cement or the adhesive; and G) allowing the cement or adhesive to harden, whereby the prosthetic teeth become solidly connected with the prosthetic base, thereby fixing the orientation and position of the prosthetic teeth to one another and to the prosthetic base, and H) separating the key from the prosthetic teeth.

2. The process according to claim 1, comprising applying before step A) a thick, fluid mass to the prosthetic base surfaces provided for fixation of the prosthetic teeth and/or the basal surfaces of the prosthetic teeth, which is arranged, after the insertion of the prosthetic teeth in step A), between the prosthetic teeth and the prosthetic base surfaces provided for fixation of the prosthetic teeth, so that the position and/or orientation of the prosthetic teeth in the prosthetic base is changeable by deformation of the thick, fluid mass.

3. The process according to claim 2, comprising removing after step D) and before step F) the thick, fluid mass from the prosthetic teeth and/or the surfaces of the prosthetic base that are provided for fixation of the prosthetic teeth.

4. The process according to claim 3, comprising removing after step D) and before step F) the thick, fluid mass from the prosthetic teeth and/or the surfaces of the prosthetic base that are provided for fixation of the prosthetic teeth by washing off with hot water or removing with steam.

5. The process according to claim 2, wherein the thick, fluid mass is a wax or a modeling clay.

6. The process according to claim 1, comprising producing and/or machining the prosthetic base and/or the prosthetic teeth with a CAM process or a rapid prototyping process.

7. The process according to claim 1, comprising in step B) directly changing the position and/or orientation of at least one prosthetic tooth in the prosthetic base by adaptation on the patient.

8. The process according claim 1, comprising, in a step E) between steps D) and F), swelling at least areas of the exposed surfaces of the prosthetic teeth with a solvent and/or swelling at least areas of the surfaces of the prosthetic base that are provided for fixation of the prosthetic teeth with a solvent.

9. The process according to claim 8, comprising, in step E), roughening and swelling at least areas of the exposed surfaces of the prosthetic teeth with a solvent and/or roughening and swelling at least areas of the surfaces of the prosthetic base that are provided for fixation of the prosthetic teeth with a solvent.

10. The process according to claim 1, wherein the surfaces of the prosthetic base that are provided for fixation of the prosthetic teeth are larger than the corresponding basal surfaces of the prosthetic teeth, so that the prosthetic teeth are tiltable and/or rotatable by up to 5°, and/or their position is displaceable by up to 1 mm in the prosthetic base.

11. The process according to claim 1, wherein the key used in step C) is a silicone key.

12. The process according to claim 1, comprising using a self-hardening cement paste as cement.

13. The process according claim 12, wherein the cement paste is made from a powder and a liquid.

14. The process according claim 12, wherein the cement paste is a polymethylmethacrylate cement dough.

15. The process according to claim 1, comprising, before step A), digitally designing a partial dental prosthesis or a total dental prosthesis using a CAD process and decomposing by file-splitting into a virtual model of a prosthetic base and a virtual model of the prosthetic teeth, wherein the prosthetic base and/or the prosthetic teeth are produced by a CAM process on the basis of the virtual models.

16. The process according to claim 1, comprising using a methyl methacrylate-containing liquid as a solvent.

17. A dental prosthesis produced with a process according to claim 1.

* * * * *